(12) United States Patent
Pajunk et al.

(10) Patent No.: US 7,027,873 B2
(45) Date of Patent: Apr. 11, 2006

(54) CATHETER FOR NEURAL BLOCKADES

(76) Inventors: Heinrich Pajunk, Am Holzplatz 5-7, D-78187 Geisingen (DE); Horst Pajunk, Am Holzplatz 5-7, D-78187 Geisingen (DE)

( * ) Notice: Subject to any disclaimer, the term of this patent is extended or adjusted under 35 U.S.C. 154(b) by 28 days.

(21) Appl. No.: 10/221,387

(22) PCT Filed: Jan. 5, 2002

(86) PCT No.: PCT/EP02/00049

§ 371 (c)(1),
(2), (4) Date: Feb. 20, 2003

(87) PCT Pub. No.: WO02/055145

PCT Pub. Date: Jul. 18, 2002

(65) Prior Publication Data

US 2003/0158592 A1     Aug. 21, 2003

(30) Foreign Application Priority Data

Jan. 11, 2001   (DE) ................ 101 00 976

(51) Int. Cl.
*A61N 1/00* (2006.01)
(52) U.S. Cl. .......................... 607/116; 604/21
(58) Field of Classification Search .................. 604/21; 607/116, 119, 120, 2, 63
See application file for complete search history.

(56) References Cited

U.S. PATENT DOCUMENTS

| 3,367,339 A | 2/1968 | Sessions |
| 4,842,585 A | 6/1989 | Witt ............................ 604/158 |
| 5,007,902 A | 4/1991 | Witt ............................ 604/117 |
| 5,081,990 A * | 1/1992 | Deletis ........................ 600/555 |
| 5,643,197 A * | 7/1997 | Brucker et al. ............... 604/20 |
| 5,782,900 A * | 7/1998 | de la Rama et al. ........ 607/122 |
| 5,800,407 A | 9/1998 | Eldor .......................... 604/264 |
| 6,080,151 A * | 6/2000 | Swartz et al. ................. 606/45 |
| 6,591,143 B1 * | 7/2003 | Ekwall ........................ 607/116 |

FOREIGN PATENT DOCUMENTS

| DE | 198 43 427 | 9/1998 |
| DE | 198 07 487 | 8/1999 |
| DE | EP 1 002 500 | 10/1999 |
| DE | AT 406 121 | 2/2000 |
| EP | 0 608 985 | 2/1997 |

OTHER PUBLICATIONS

Polymedic Stimcath. Stimcath monopolar.

* cited by examiner

*Primary Examiner*—Mark Bockelman
(74) *Attorney, Agent, or Firm*—O'Shea, Getz & Kosakowski, P.C.

(57) ABSTRACT

The invention relates to a catheter (10) for neural blockades in anaesthesia. Said catheter consists of a flexible plastic tube in which a wire (16) is arranged for electrostimulation. The distal end of said wire (16) is conductively applied to a contact tip protruding out of the catheter (10). Said contact tip consists of a stopper (12) and a cap (14) which are positioned in the catheter (10), the cap being arranged in front of the distal end of said catheter (10) and covering the edge of the front surface thereof.

8 Claims, 2 Drawing Sheets

CATHETER FOR NEURAL BLOCKADES

BACKGROUND OF THE INVENTION

The present invention relates to the field of catheters, and in particular to a catheter for nerve blocks in anesthesia.

In anesthesia, for lengthy operations, postoperative pain therapy, and treatment of chronic pain states, the nerves supplying a specific region of the body are often blocked by an anesthetic. A catheter is used to introduce the anesthetic, and the distal end of the catheter is positioned as close as possible to the nerve to achieve an optimum effect with a minimal quantity of anesthetic. The catheter, which can remain in position for a long time if necessary, includes a long, thin, flexible plastic tube.

To insert the catheter into the sheath or canal of the nerve, a cannula is used to insert the catheter. U.S. Pat. No. 5,007,902 teaches replacement of such a cannula by a puncture cannula, in which case the puncture cannula is pulled away in order to insert the catheter. German patent DE 3643235 C1 teaches a puncture cannula whose internal canal emerges at the side behind the distal tip of the cannula, with the catheter being inserted and positioned by means of this puncture cannula. Once the catheter is in position, the cannula used for its insertion is removed.

U.S. Pat. No. 5,007,902 also teaches the use of electrical nerve stimulation for precise positioning of the catheter. In this case, a guide wire is inserted in the catheter, and its distal end protrudes slightly from the distal end of the catheter. The proximal end of the guide wire is electrically contactable for connection of a stimulator. Using electrical simulation, the position of the distal end of the catheter can be determined exactly while the catheter is being inserted into the sheath or canal of the nerve. Since the guide wire completely fills the internal cross section of the catheter, the wire has to be removed from the catheter as soon as the catheter is in place in order to apply the anesthetic through the catheter. If the catheter remains in place for a long period of time and further medication has to be introduced, it is often necessary to check the position of the catheter and possibly correct it. It is necessary for this purpose to insert a guide wire once again to determine the position of the distal end of the catheter by electrical stimulation.

It is also known that a thin wire can be disposed in the catheter for electrical stimulation, the cross section of which is smaller than the free internal cross section of the catheter. In this way, the wire does not impede introduction of a liquid through the catheter so that the wire can remain in the catheter. The position of the wire, fixedly disposed in the catheter, can be checked by electrical stimulation and corrected for the entire time that it is in place. However, if the thin end of the wire protrudes from the distal end of the catheter, there is a risk that the tip of the wire may cause damage and injury to the nerves while the catheter is being pushed forward. If the wire does not protrude from the distal end of the catheter, although this risk is reduced the electrical contact for electrical stimulation is no longer reliably assured.

Therefore, there is a need for a catheter for a nerve block that can be positioned by electrical stimulation, ensuring a reliable contact for electrical stimulation and a minimal risk of injury, and making it possible for the catheter position to be checked at any time by electrical stimulation.

SUMMARY OF THE INVENTION

A contact tip is placed in the distal end of the catheter, comprising a metal part inserted coaxially with a plug into the distal end of the catheter, protruding with a cap at the distal end of the catheter, and overlapping the edge surface thereof. For an electrically conductive connection between this contact tip and the proximal end, a thin wire is disposed in the catheter which is connected in an electrically conducting fashion with the plug of the contact tip. The contact tip with its cap forms the distal end of the catheter. The cap provides a reliable electrical contact over a large surface area for nerve stimulation. The blunt, rounded cap overlapping the distal end of the catheter also avoids the risk of injuring the nerve as the catheter slides forward. The plug inserted into the distal end of the catheter keeps the contact tip centered in the distal end of the catheter. The thin wire passing through the catheter in order to connect the distal contact tip with the proximal connector of the stimulator does not prevent a liquid such as an anesthetic from being introduced. Electrical stimulation is possible as the catheter is being inserted for exact positioning and can be repeated at any time while the catheter is in place to check, and if necessary correct, its position.

The contact tip can completely close off the distal end of the catheter. In this case, the liquid introduced through the catheter exits distally through outlet openings provided in the catheter wall at its distal end area immediately behind the contact tip. In another embodiment, the contact tip can have an axial hole through which the liquid can pass. In this case, outlet openings in the catheter wall are not necessary, but can be provided in order to enlarge the outlet cross section. The outlet openings in the catheter wall are preferably formed so that, with their center axis, that is the outlet direction, they form an acute angle of less than 90° with the center axis of the catheter, with this acute angle opening in the distal direction. The acute angle can be approximately 45° in one preferred embodiment. The shape of the outlet openings at an angle in the forward direction causes the liquid introduced through the catheter to exit in the distal direction so that the liquid, for example an anesthetic, is precisely applied.

These and other objects, features and advantages of the present invention will become more apparent in light of the following detailed description of preferred embodiments thereof, as illustrated in the accompanying drawings.

DETAILED DESCRIPTION OF THE INVENTION

Figure 1:
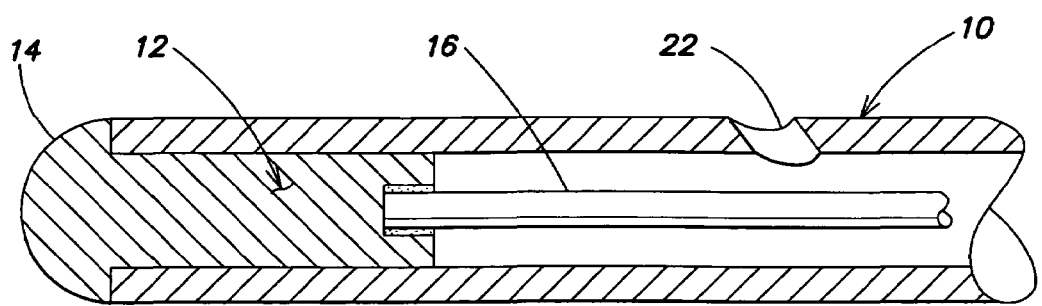
FIG. 1 is an axial section through the distal end of the catheter in a first embodiment.

FIG. 1 is a cross section view of a catheter 10. The catheter 10 is a flexible tube, made for example of plastic or polyamide. The length of the catheter 10 depends on its application. For peripheral plexus anesthesia, the length of the catheter 10 is approximately 400 mm, while for peridural and spinal anesthesia a length of for example 900 mm may be used. The diameter of the catheter 10 also depends on the application. For example, a 19 G catheter has an external diameter of 1 mm and an internal diameter of 0.5 mm. A 20 G catheter has an external diameter of 0.8 mm and an internal diameter of 0.4 mm. It is possible to use a still thinner catheter with correspondingly smaller diameters.

The catheter 10 includes a contact tip that is placed in the distal end of the catheter 10, and is formed as a metal part. The contact tip includes a plug 12 and a cap 14, in one piece. The plug 12 has the shape of a circular cylinder whose external diameter corresponds to the internal diameter of the catheter 10. This makes it possible to insert the plug 12 of the contact tip into the distal end of the catheter 10 so that the plug 12 is held with a snug fit in the catheter 10. The external diameter of the cap 14 corresponds to the external diameter of the catheter 10. When the contact tip is inserted into the distal end of the catheter 10, the plug 12 is pushed into the lumen of the catheter 10 until the cap 14 abuts the distal end surface of the catheter 10. Since the diameter of the plug 12 corresponds to the internal diameter of the catheter 10, the plug 12 holds the contact tip in the center at the distal end of the catheter 10 with the cap 14 overlapping and covering the edge surface of the catheter 10. At the outer periphery, the cap 14 fits flush to the catheter 10 so that the cap 14 fits seamlessly into the outer periphery of the catheter 10.

For an electrically conductive connection of the contact tip with a stimulator (not shown) connected at the proximal end of the catheter, a thin wire 16 is disposed in the catheter 10. The diameter of the wire 16 is considerably smaller than the internal diameter of the catheter 10, so that a considerable portion of the lumen of the catheter 10 remains free for a liquid to pass through. The diameter of the wire 16 is for example 0.2 mm. The proximal end of the wire 16 is contactable with the stimulator in a manner not shown. The distal end of the wire 16 is connected in an electrically conducting fashion with the plug 12 of the contact tip, for example soldered, glued, embossed, or laser-welded. A number of embodiments of the contact tip are described below.

In the embodiment of FIG. 1, the plug 12 and the cap 14 are closed. The cap 14 is in the shape of a hemisphere whose curved portion is on the distal side. The wire 16 is soldered coaxially into a blind hole provided coaxially in the inside end surface of the plug 12.

Figure 2:
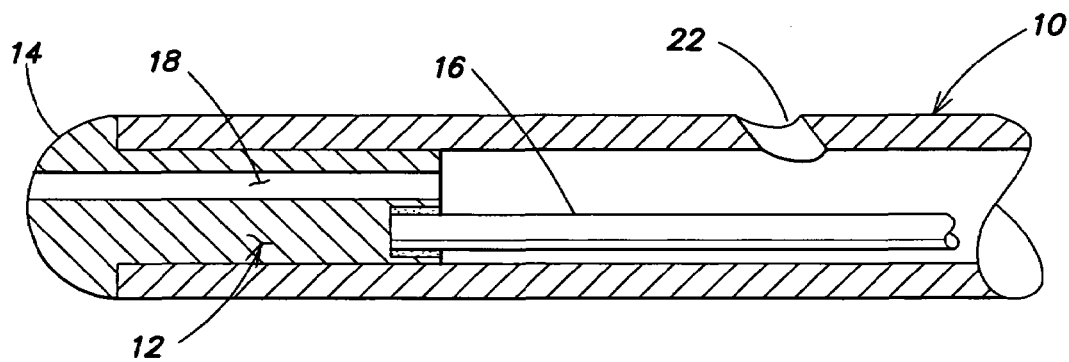
FIG. 2 is a corresponding view of a second embodiment.

In the embodiment of FIG. 2, the cap 14 is also in the shape of a hemisphere. A through-hole 18 passes through the contact tip (i.e., through the plug 12 and the cap 14), and runs eccentrically and axially parallel thereto. The blind hole that receives the wire 16 is located axially parallel and externally diametral to the through-hole 18.

Figure 3:
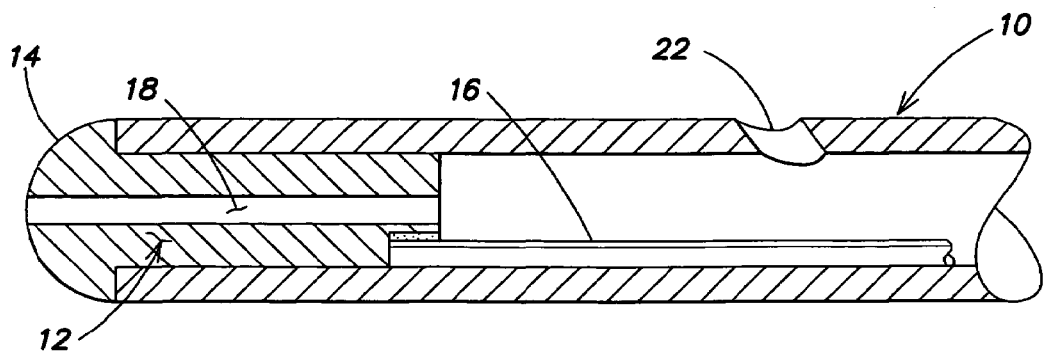
FIG. 3 is a corresponding view of a third embodiment.

In the embodiment of FIG. 3, the cap 14 is also hemispherical. The through-hole 18 passes coaxially through the plug 12 and the cap 14. The wire 16 is soldered into a groove formed axially in the outer periphery of the plug 12.

Figure 4:
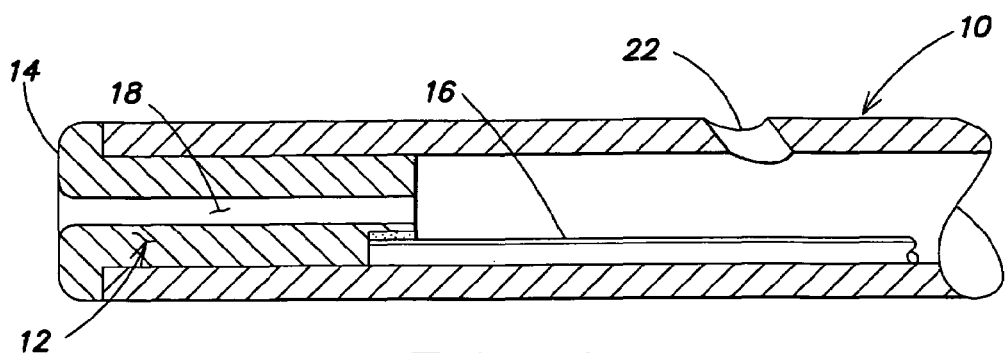
FIG. 4 is a corresponding view of a fourth embodiment.

In the embodiment of FIG. 4, the cap 14 is in the shape of a flat plate that extends from a smooth distal end surface starting at the outer circumference with a radius of curvature and makes a transition to the cylindrical circumferential surface of the catheter 10. As in the embodiment of FIG. 3, the through-hole 18 is coaxial and the wire 16 is set in an axial circumferential groove.

Figure 5:
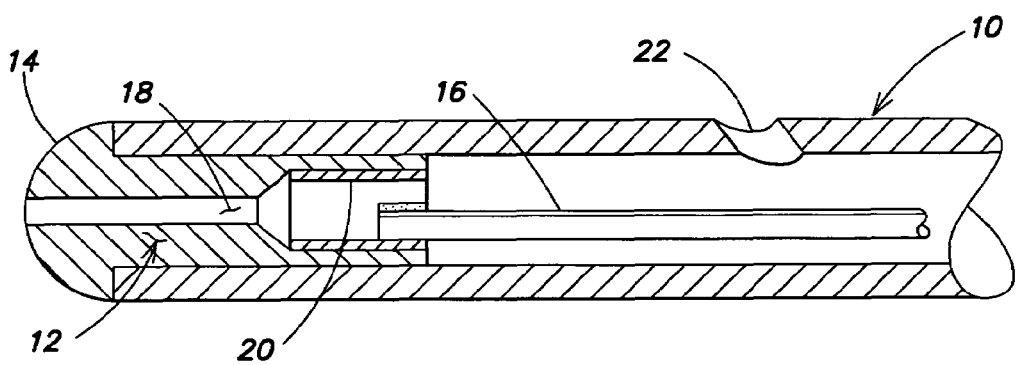
FIG. 5 is a corresponding view of a fifth embodiment.

In the embodiment of FIG. 5, the cap 14 is in the shape of a hemisphere. The through-hole 18 is coaxial, and has a larger diameter toward the inside end of the plug 12. A hollow bushing 20 is inserted into this enlarged section of through-hole 18, and includes an inside wall to which the wire is electrically connected.

If the contact tip has an axial through-hole 18, a liquid such as an anesthetic can be added through the catheter 10 and exit through this through-hole 18. If the contact tip is closed, as for example in the embodiment of FIG. 1, one or more outlet openings 22 are provided in the distal end area of the catheter 10 behind the contact tip, through which openings the liquid can exit. Such outlet openings 22 can also be provided in cases where the contact tip has an axial through-hole 18 to enlarge the cross section for the added liquid to exit.

Figure 6:
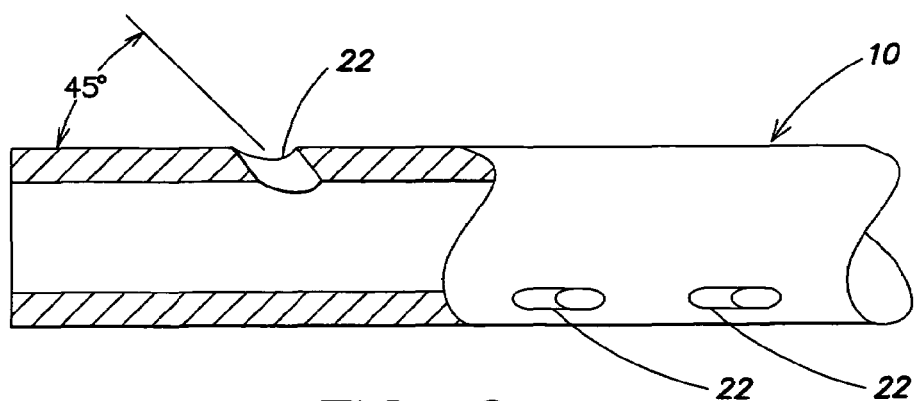
FIG. 6 is a lateral view of the distal end of the catheter without the contact tip, in partial axial section.

The outlet openings 22 may have any shape, cross section, and arrangement. A design such as that shown in FIG. 6 is preferable. In this design, the outlet openings 22 are provided in the wall of the catheter 10 such that the center axis of the outlet opening 22 makes an acute angle with the center axis of the catheter 10 (e.g., an angle of 45°), with this acute angle opening in the distal direction. In this way, the liquid added is directed distally through the outlet openings 22. Three outlet openings 22 are provided, making angles of 120° with each other in the circumferential direction. This ensures that the liquid added is dispensed evenly over the entire periphery of the distal end of the catheter 10. In order for the outlet openings 22 not to weaken the wall of the catheter 10, the outlet openings 22 are preferably offset axially from each other.

Although the present invention has been shown and described with respect to several preferred embodiments thereof, various changes, omissions and additions to the form and detail thereof, may be made therein, without departing from the spirit and scope of the invention.

What is claimed is:

1. A catheter for a nerve block in anesthesia comprising:
   a flexible plastic tube that forms a lumen and includes a tube proximal end and a tube distal end;
   a wire in said catheter for electrical stimulation, whose wire proximal end is electrically contactable at the tube proximal end and which leads to a contact tip protruding distally from said catheter, where the contact tip is a metal part that includes a plug and a cap, wherein said plug is insertable coaxially into the distal end of said catheter, that said cap is disposed in front of said tube distal end and overlaps its distal edge surface, that the cross section of said wire is smaller than the free internal cross section of said catheter, and said wire is connected in an electrically conducting fashion at its wire distal end with said plug, wherein the wall of said catheter has at least one outlet opening at its distal end area behind said plug and the center axis of the at least one liquid outlet opening makes an acute angle of less than 90° with respect to the center axis of said catheter in the distal direction, whereby fluid injected into the proximal end of the tube is directed generally in the distal direction.

2. The catheter of claim 1, wherein said plug and said cap form a single metal part.

3. The catheter of claim 2, wherein said wire is soldered, glued, embossed, or laser-welded to said plug.

4. The catheter of claim 3, wherein said cap is blunt and rounded, and makes a smooth transition at its outer periphery into the outer contour of said catheter.

5. The catheter of claim 4, wherein said cap is in the shape of a hemisphere.

6. The catheter of claim 4, wherein through-hole passes axially through said plug and said cap.

7. The catheter of claim 1, wherein said at least one outlet opening comprises three outlet openings offset by 120° in the circumferential angle, and offset axially to each other.

8. The catheter claim 1, wherein said at least one outlet opening comprises three outlet openings offset by 120° in the circumferential direction, and offset axially to each other.

* * * * *

UNITED STATES PATENT AND TRADEMARK OFFICE
CERTIFICATE OF CORRECTION

PATENT NO. : 7,027,873 B2
DATED : April 11, 2006
INVENTOR(S) : Pajunk et al.

It is certified that error appears in the above-identified patent and that said Letters Patent is hereby corrected as shown below:

Column 5,
Line 58, after "wherein" insert -- a --.
Line 63, after "catheter" insert -- of --.

Signed and Sealed this

Thirtieth Day of May, 2006

JON W. DUDAS
*Director of the United States Patent and Trademark Office*